United States Patent
Kirchhoff et al.

(10) Patent No.: US 10,480,001 B2
(45) Date of Patent: Nov. 19, 2019

(54) METHOD FOR THE GENERATION OF A MONOCLONAL PLANT CELL LINE

(75) Inventors: Janina Kirchhoff, Aachen (DE); Stefan Schillberg, Aachen (DE); Andreas Schiermeyer, Köln (DE); Helga Schinkel, Aachen (DE); Rainer Fischer, Aachen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 125 days.

(21) Appl. No.: 14/115,629

(22) PCT Filed: Jun. 7, 2011

(86) PCT No.: PCT/EP2011/002785
§ 371 (c)(1),
(2), (4) Date: Nov. 4, 2013

(87) PCT Pub. No.: WO2012/167803
PCT Pub. Date: Dec. 13, 2012

(65) Prior Publication Data
US 2014/0053300 A1 Feb. 20, 2014

(51) Int. Cl.
C12N 15/82 (2006.01)
A01H 4/00 (2006.01)

(52) U.S. Cl.
CPC ......... *C12N 15/8241* (2013.01); *A01H 4/005* (2013.01)

(58) Field of Classification Search
None
See application file for complete search history.

(56) References Cited

U.S. PATENT DOCUMENTS

| 4,300,310 A | 11/1981 | Galbraith |
| 2008/0098495 A1 | 4/2008 | Olesen et al. |

OTHER PUBLICATIONS

IBargmann et al (Positive Fluorescent Selection Permits Precise, Rapid, and In-Depth Overexpression Analysis in Plant Protoplasts. Plant).*
Yoo et al (Arabidopsis mesophyll protoplasts: a versatile cell system for transient gene expression analysis. Nature Protocols vol. 2 No. 7, 1565-1573, 2007).*
Eigel et al (Nurse Culture of Individual Cells: Regeneration of Colonies from Single Protoplasts of Nicotiana tabacum, *Brassica napus* and Hordeum vulgare. J. Plant Physiol. vol. 134. pp. 577-581, 1989).*
Santos et al (Putting the Spotlight Back on Plant Suspension Cultures Frontiers in Plant Science , 7: 1-12, 2016).*
Kirchhoff et al (Monoclonal tobacco cell lines with enhanced recombinant protein yields can be generated from heterogeneous cell suspension cultures by flow sorting. Plant Biotechnology Journal. 10, pp. 936-944, 2012, p. 936, left col, 1st and 2nd para; right col, 1st para).*
Schaffler et al (Single Cell Nurse Culture of Tobacco Protoplasts: Physiological Analysis of Conditioning Factors. J. Plant Physiol. vol. 137. pp. 95-101, 1990).*
Bargmann et al (Positive Fluorescent Selection Permits Precise, Rapid, and In-Depth Overexpression Analysis in Plant Protoplasts. Plant Physiology, vol. 149, pp. 1231-1239, Mar. 2009).*
Herzenberg et al (The History and Future of the Fluorescence Activated Cell Sorter and Flow Cytometry: A View from Stanford. Clinical Chemistry 48:10, 1819-1827, 2002).*
Raveh et al (In vitro culture of tobacco protoplasts: Use of feeder techniques to support division of cells plated at low densities. In vitro. 9(3): 216-222, 1973).*
Nocarova et al (Cloning of transgenic tobacco BY-2 cells; an efficient method to analyse and reduce high natural heterogeneity of transgene expression. BMC Plant Biology 2009, 9:44,1-11, published Apr. 2009). (Year: 2009).*
Eigel L et al: "Nurse Culture of 6,7 Individual Cells Regeneration of Colonies From Single Protoplasts of Nicotiana-Tabacum *Brassica-napus* and Hordeum-Vulgare". Journal of Plant Physiology. Fischer. Stuttgart. DE. vol. 134. No. 5. Jan. 1, 1989 (Jan. 1, 1989). pp. 577-581. XP009151889.
Schaeffler E et al: "Single Cell Nurse Culture of Tobacco Protoplasts Physiological Analysis of Conditioning Factors", Journal of Plant Physiology, Fischer, Stuttgart, DE, vol. 137, No. I, Jan. 1, 1990 (Jan. 1, 1990), pp. 95-101, XP009151890, ISSN: 0176-1617.
Galbraith D W et al: 11 Flow Sorting and Culture of Protoplasts Conditions for High-Frequency Recovery Growth and Morphogenesis From Sorted Protoplasts of Suspension Cultures of Nicotiana-Tabacum Cultivar Wisconsin-38, Plant Cell Reports, vol. 3, No. 4, 1984, pp. 151-155, XP009155589, ISSN: 0721-7714.
B. O.R. Bargmann et al: "Positive Fluorescent Selection Permits Precise, Rapid, and In-Depth Overexpression Analysis in Plant Protoplasts", Plant Physiology, vol. 149, No. 3, Mar. 1, 2009 (Mar. 1, 2009) , pp. 1231-1239, XP55016770, ISSN: 0032-0889, DOI: 10.1104/pp.108.133975.
Kristi R. Harkins et al: "Flow sorting and culture of plant protoplasts", Physiologia Plantarum, vo 1. 60, No. I, Jan. 1, 1984 (Jan. 1, 1984), pp. 43-52, XP55016786, ISSN: 0031-9317, DOI: 10.1111/j.1399-3054.1984. tb04247.x.

(Continued)

*Primary Examiner* — Medina A Ibrahim
*Assistant Examiner* — Wayne Zhong
(74) *Attorney, Agent, or Firm* — Saffire IP; Darren P. Nicholson

(57) ABSTRACT

The invention provides a method for the generation of a monoclonal plant cell line from a heterologous population of plant cells, comprising the following steps: (a) provision of a heterologous population of plant cells; (b) preparation of protoplasts from said heterologous population of plant cells; (c) separation of single protoplasts by subjecting the preparation of protoplasts to flow cytometric sorting; (d) regeneration of a separated single transformed protoplast until the formation of a microcolony by co-cultivation in the presence of feeder cell material; (e) removal of the microcolony from the feeder cell material and cultivation of the microcolony until the formation of a monoclonal plant cell line.

9 Claims, 1 Drawing Sheet

(56) References Cited

OTHER PUBLICATIONS

Glimelius K. et al: "Sel ection and enrichment of plant protoplast heterokaryons of Brassicaceae by flow sorting", Plant Science, Elsevier Ireland Ltd, IE, vo 1.45, No. 2, Jan. 1, 1986 (Jan. 1, 1986), pp. 133-141, XP023472024, ISSN: 0168-9452, DOI: 10.1016/0168-9452(86)90049-X [retrieved on Jan. 1, 1986].
Sangthong Ratchada et al: "Gametosomatic hybridization between egg cell protoplast and mesophyll protoplast of Petunia hybri da" ,Plant Biotechnology, vol. 26, No. 4, Sep. 2009 (Sep. 2009), pp. 377-383 URL, XP002669917, ISSN: 1342-4580.
Michael C Naill et al: "Culture of Isolated Single Cells from Taxus Suspensions for the Propagation of Superior Cell Populations", Biotechnology Letters, Springer Netherlands, Dordrecht, vol. 27, No. 21, Nov. 1, 2005 (Nov. 1, 2005), pp. 1725-1730, XP019231032, ISSN: 1573-6776, DOI: 10.1007/S10529-005-2738-1.
Von Keller Angnes et al: "Influence of electrical treatment and cell fusion on cell proliferation capacity of sunflower protoplasts in very low density culture", Plant Science (SHANNON), vol. 126, No. I, 1997, pp. 79-86, XP002669918, ISSN: 0168-9452.
A. Suzuki et al: "Prospective Isolation of Multipotent Pancreatic Progenitors Using Flow-Cytometric Cell Sorting", Diabetes, vo 1. 53, No. 8, Jan. 1, 2004 (Jan. 1, 2004), pp. 2143-2152, XP55016787, ISSN: 0012-1797, DOI: 10.2337/diabetes.53.8.2143.
Galbraith: "Flow cytometry and cell sorting: The next generation", Methods, vol. 57, pp. 249-250 (2012).
Santos et al., "Putting the Spotlight Back on Plant Suspension Cultures," Frontiers in Plant Science, Mar. 2016, vol. 7, Article 297.
Frenzel et al. "Expression of recombinant antibodies," Frontiers in Immunology, Jul. 2013, vol. 4, Art. 217.
Nocarova et al., "Cloning of transgenic tobacco BY-2 cells; an efficient method to analyse and reduce high natural heterogeneity of transgene expression," BMC Plant Biology (2009) vol. 9,44.
Galbraith et al., "Flow sorting and culture of protoplasts: Conditions for high-frequency recovery, growth and morphogenesis from sorted protoplasts of suspension cultures of nicotiana," Plant Cell Reports (1984) 3: pp. 151-155 (only first two pages submitted, full paper previously submitted in IDS of Nov. 4, 2013).
Galbraith, D., "Flow cytometry and cell sorting: The next generation," Methods (2012) vol. 57, pp. 249-250.
Qu et al., "[Effect of homogeneity on cell growth and anthocyanin biosynthesis in suspension cultures of Vitis vinifera]," Abstract, Sheng Wu Gong Cheng Xue Bao. Sep. 2006;22(5):805-10. [Article in Chinese].
Qu et al., "Instability of anthocyanin composition under different subculture conditions during long-term suspension cultures of *Vitis vinifera* L. var. Gamay Fréaux," Abstract, Sheng Wu Gong Cheng Xue Bao. Nov. 2011;27(11):1613-22.
Kirchhoff et al., "Monoclonal tobacco cell lines with enhanced recombinant protein yields can be generated from heterogeneous cell suspension cultures by flow sorting," Plant Biotechnology Journal (2012) 10, pp. 936-944.
Ganapathi et al., "Tobacco (*Nicotiana tabacum* L.)—A model system for tissue culture interventions and genetic engineering," Indian Journal of Biotechnology, vol. 3, Apr. 2004, pp. 171-184.
Plant Cell Culture Protocols, ed. Loyola-Vargas and Ochoa-Alejo, Humana Press, Springer Protocols, 2012.

\* cited by examiner

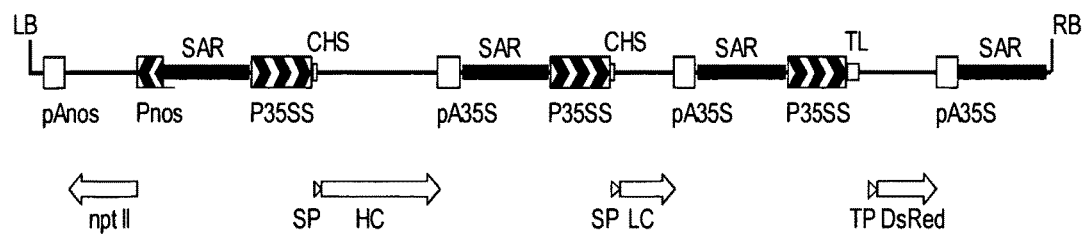

METHOD FOR THE GENERATION OF A MONOCLONAL PLANT CELL LINE

TECHNICAL FIELD

The present invention relates to the field of plant biotechnology. In particular, the present invention relates to the generation of a native (wild-type) or transgenic monoclonal plant cell line from a heterogeneous population of plant cells through flow cytometric sorting. As will be apparent for a skilled person, the invention also comprises to use the monoclonal plant cell line for the regeneration of whole fertile plants.

BACKGROUND OF THE INVENTION

During the past decades, enormous efforts have been dedicated to the establishment and culturing of plant-based systems for the accumulation and harvesting of native or heterologous proteins and secondary metabolites. The literature provides a vast quantity of evidential material that proves the utility of plant-based systems to produce a large variety of desired substances that are either secreted into the culture medium or isolated from the producing cells, tissues, organelles or even whole plants or parts thereof. Likewise, a broad range of transformation protocols exist that ensure the establishment of either stably or transiently transformed plant material. However, there is still a need for a reliable, relatively cost-efficient and rapid technology to obtain high yields of a desired product from plant cells.

It has been repeatedly reported that transformation of a population of plant cells such as a plant suspension culture frequently results in transgenic cultures that exhibit cells with highly heterogeneous (mixed) and inconsistent expression levels of the target protein related to the mixture of epigenetically different cells within the primary heterogeneous cell population. Within recombinant cell lines the heterogeneity in transgene expression demonstrates a serious problem in terms of production rates.

A main problem is that high-producing clones are often rare events within a transformation assay and it is very time consuming to establish a homogeneous high-producing cell line. A still ongoing technical challenge, therefore, is the elite transgenic event production and recovery from a freshly transformed or already transgenic plant culture.

For flow cytometric sorting such as e.g. FACS application, single spherical cells must be obtained from the usually aggregated plant cell population or culture by enzymatic digestion of the cells to liberate protoplasts. For most plant species, however, the regeneration of single protoplasts is hampered by the necessity to be maintained at certain population densities.

A reliable and reproducible procedure for the regeneration of a single transgenic cell/protoplast or for the regeneration of a whole fertile plant therefrom (especially after flow cytometric sorting) has hitherto not been described.

SUMMARY OF THE INVENTION

The present invention is thus primarily concerned with the provision of a plant-based system to produce high levels of desired native or recombinant products that makes use of a non-transformed or transgenic monoclonal plant cell line generated from a heterogeneous (mixed) population of plant cells such as a suspension culture and overcomes the problems of the prior art, in particular with respect to the rapid separation and subsequent regeneration of single (transgenic) protoplasts until the formation of a microcolony that can be used to establish a monoclonal plant cell line that, preferably, is capable of producing and accumulating high quantities of the desired product. It is clear for a skilled person that the present invention likewise enables to provide whole fertile plants regenerated from the established monoclonal plant cell line.

Contrary to many currently used and developed systems that are based on the use of intact plants or at least intact and differentiated plant tissue, the use of suspension cells has the advantage that homogeneous material can be reproducibly produced under controlled, aseptic and contained conditions.

There are currently two principal strategies to produce recombinant proteins in plants, namely (i) the generation of stable transgenic plants or suspension cell lines or (ii) the transient expression of heterologous gene(s) after infecting the plant expression hosts (plant, tissue or cells) with a bacteria (e.g. *Agrobacterium*), a virus (e.g. Tobacco mosaic virus, Potato virus X/Y, Cowpea mosaic virus and many others), or a combination of both (e.g. magnifection) to enable the host to express the heterologous genetic information (DNA or RNA). In the alternative and as known in the art, the genetic information can also be introduced into the plant expression host by established mechanical means such as e.g. electroporation or laser perforation.

Although the invention is preferably concerned with the use of stably transformed plant cell material, systems for the transient expression having the advantage of speed (gene-to-product, time-to-market, emergency response) as well as the possibility to achieve accumulation levels that are much higher than those that can typically be obtained in stably transformed transgenic plants or parts thereof such as cells may also be involved in the method according to the present invention.

According to the invention, there is provided a method for the generation of a native (wild-type, non-transformed) or transgenic monoclonal plant cell line from a heterogeneous population of plant cells. The method comprises to firstly provide said population of plant cells such as e.g. plant suspension cells forming the source plant cell material that is subjected to the further steps comprised by the method according to the invention. Usually, this plant cell material can easily be derived from e.g. a heterogeneous plant suspension culture which, preferably, has been cultivated under controlled and/or aseptic conditions. The source cells can be (stably/transiently) transformed transgenic cells or wild-type (native, non-transformed) cells able to produce and accumulate a desired product.

Since the method according to the invention uses flow cytometric sorting such as e.g. FACS technology to separate or isolate single, i.e. individualized protoplasts, these have to be prepared from a population of plant cells as provided above using materials and methods known in the art. According to a preferred embodiment, these protoplasts are transformed and capable of (i) producing a fluorescent marker protein or polypeptide, (ii) producing a desired product, and/or (iii) surviving in presence of a selection agent. The preferred sorting criteria for flow cytometric sorting are cell granularity as a marker for e.g. qualitative characteristics such as apoptosis, and cell size. The preferred sorting criteria for FACS can be selected from the group comprising the genetic background (e.g. ploidy, aneuploidy), mutants transgenics, gene exchange products, and fluorescence (e.g. autofluorescence (chloroplasts, metabolites), fluorescent proteins or enzyme-mediated fluorescence). It is to be understood that the use of a selection agent is not necessary. Thus, the protoplast does not necessarily have to be transformed with a nucleic acid sequence conferring an appropriate resistance.

After the separation or isolation of single (transformed) protoplasts by flow cytometric sorting such as e.g. FACS, each single transformed protoplast is regenerated until the formation of a microcolony (microcallus) by co-cultivation in the presence of feeder cell material. The plant source origin is not limited but restricted to those lines, varieties and species whose protoplasts have the potential to regenerate until the formation of a microcolony or microcallus. The present invention is thus applicable to all plant varieties and species for which a regeneration protocol has been established or will be provided in the future. In view of the aspect according to the invention concerning the further regeneration of the monoclonal microcolony or plant cell line into whole fertile plants, it is to be understood that this aspect can be carried out with all plant varieties and species for which a regeneration protocol has been established or will be provided in the future.

Subsequently, the microcolony is separated or removed from the feeder cell material and cultivated until the formation of a monoclonal plant cell line.

According to a preferred embodiment, the next step comprised by the method according to the invention therefore relates to the generation of a monoclonal callus tissue by (i) transferring the microcolony or microcallus to solid cultivation medium and (ii) cultivating the microcolony or microcallus in the presence of at least one selection agent until the formation of a transgenic callus tissue from which a transgenic monoclonal plant cell line can be established by transferring the callus tissue to liquid cultivation medium. As will be appreciated by the skilled person, the microcolony can also be removed or separated from the feeder cell material by mechanical means such as e.g. by clone picking. In this case, no selection agent is needed and the cells comprised by the microcolony do not need to display resistance against any selection agent.

According to a preferred embodiment, the cells comprised by the heterogeneous population of plant cells are native (e.g. wild-type) or non-transgenic cells that, before being subjected to flow cytometric sorting, are stably or transiently transformed with at least one expression vector comprising at least one heterologous nucleic acid sequence operably linked to a functional promoter, wherein said at least one heterologous nucleic acid sequence codes for a desired product. According to a further embodiment, the at least one expression vector comprises at least two heterologous nucleic acid sequences operably linked to (a) functional promoter(s), wherein said at least two heterologous nucleic acid sequences code for a fluorescent marker protein or polypeptide and for a resistance against a selection agent or for a desired product. If desired, the cells may additionally comprise a heterologous nucleic acid sequence that codes for a desired product to be accumulated in the transgenic monoclonal plant cell line as provided according to the invention.

The term "heterologous" as used herein indicates that the gene/sequence of nucleotides in question have been introduced into plant cells by using genetic engineering, i.e. by human intervention. A heterologous sequence of nucleotides may comprise the coding sequence for a fusion protein comprised of a fusion partner that may be formed, for example, in part by a plant protein that may be fused to a non-plant protein which may be termed a hybrid plant:non-plant fusion protein for the purposes of the present invention. Alternatively, a fusion protein may be one which is formed of fusion partners that are of non-plant origin. A heterologous gene may augment the expression of a protein of interest from an endogenous equivalent gene, i.e. one which normally performs the same or a similar function, or the inserted sequence may be additional to the endogenous gene or other sequence. Nucleic acid heterologous to a cell may be non-naturally occurring in the cultivated cell type, variety or species. Thus, the heterologous nucleic acid may comprise a coding sequence of, or derived from, a particular type of organism, such as a plant or mammalian species, e.g. of human, ovine, bovine, equine, or porcine species, placed within the context of a cultivated cell such as a BY2 cell derived from tobacco. A further possibility is for a nucleic acid sequence to be placed within a cultivated target cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. Furthermore, synthetic (artificial) nucleic acid sequences can be used as well.

"Vector" is defined to include, inter alia, any plasmid, cosmid, phage, or viral vector in double or single stranded linear or circular form which may or may not be self transmissible or mobilizable, and which can transform a prokaryotic or eukaryotic host and exists extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, mosses, mammalian, yeast or fungal) cells.

"Expression vector" refers to a vector in which a nucleic acid is under the control of, and operably linked to, an appropriate promoter or other regulatory elements for transcription in a host cell such as a microbial or plant cell. The vector may be a bi-functional expression vector which functions in multiple hosts. In the case of genomic or subgenomic DNA, this may contain its own promoter or other regulatory elements and in the case of cDNA this may be under the control of an appropriate promoter or other regulatory elements for expression in the host cell.

A "promoter" is a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

The invention also embraces use of a variant of any of these sequences. A variant protein shares homology with, or is identical to, all or part of the sequences discussed above.

For the expression of recombinant proteins, a suspension of recombinant Agrobacteria or viruses (vectors) containing the genetic information for the proteins of interest is applied to the plant suspension cells mentioned above in a manner known in the art. The vector infects the plant cells and transmits the genetic information. Preferably, the plant cell material to be transformed is provided in high density with only small amounts of media being present so that the vector suspension can be applied just by dropping or spraying. This preferred embodiment of transformation has several practical advantages with respect to handling, automation, containment, up-scaling and waste production and removal. In the alternative, known techniques such as particle bombardment, electroporation and the like can be used as known in the art.

Suitable promoters include the Cauliflower Mosaic Virus 35S (CaMV 35S). The promoter may be selected to include one or more sequence motifs or elements conferring developmental and/or tissue-specific regulatory control of expression.

As already mentioned, the at least one selectable genetic marker, that may be desired to be produced, may be included in the construct or be provided in a second construct, such as those that confer selectable phenotypes such as resistance to antibiotics or herbicides (including but not limiting e.g. kanamycin, hygromycin, phosphinotricin, chlorsulfuron, methotrexate, gentamycin, spectinomycin, imidazolinones and glyphosate).

Alternatively, the plant suspension cells used for the preparation of protoplasts can also be provided from an already transgenic heterogeneous plant suspension culture comprising transgenic cells.

The (transgenic) monoclonal plant cell line established according to the invention can be treated or cultivated in the presence of precursors, inducers, hormones, stabilizers (e.g. compatible solutes), inhibitors, RNAi/siRNA molecules, signaling compounds, enzymes (e.g. pectinase), and/or elicitors in addition to or instead of the vector suspension, for the production of recombinant proteins or metabolites.

According to a preferred embodiment, the desired product is selected from the group consisting of heterologous proteins or polypeptides (e.g. blood products, cytokines, growth hormones, therapeutic/diagnostic/industrial enzymes, vaccines, full-size antibodies or various antibody derivates), secondary metabolites (e.g. Phenylpropanoids, Alkaloids, Terpenoids, Quinones or Steroids), and markers for the diagnosis or analysis of gaseous, solid or fluidic (chemical) compounds and substances.

Genes of interest include those encoding proteins which are themselves natural medicaments such as pharmaceuticals or veterinary products. Furthermore, genes of interest also include any other recombinant protein such as e.g. technical enzymes, toxins, or recombinant proteins conferring for new agronomic input and output traits.

Heterologous nucleic acids may encode, inter alia, genes of bacterial, fungal, plant or non-plant origin such as fusion proteins as alluded to hereinabove or animal origin. Polypeptides produced may be utilized for producing polypeptides which can be purified therefrom for use elsewhere. Proteins that can be produced in a process of the invention include heterodimers, such as FSH, immunoglobulins, fusion antibodies and single chain antibodies. Furthermore, the above genes may be altered to produce proteins with altered characteristics such as a modified glycane structure. However, the invention does also allow to use synthetic genes such as artificial sequences that, as such, do not exist in nature.

Such proteins include, but are not limited to retinoblastoma protein, p53, angiostatin, and leptin. Likewise, the methods of the invention can be used to produce mammalian regulatory proteins. Other sequences of interest include proteins, hormones, such as follicle stimulating hormone, growth factors, cytokines, serum albumin, hemoglobin, collagen, thaumatin, thaumatin-like proteins, epidermal growth factors such as VEGF, etc.

As will be appreciated by the skilled artisan, the invention enables to produce a large variety of proteins and polypeptides including (recombinant) proteins of pharmaceutical relevance (such as e.g. vaccines, antibodies, therapeutical enzymes, allergens and hypoallergens, antimicrobial peptides, structural proteins such as elastin and collagen for use as biocompatible coating materials, virus-like particles, protein bodies etc.), (recombinant) proteins of nutritional value (food and feed additives), (recombinant) proteins for diagnostic applications (such as e.g. enzymes, antibodies and engineered antibodies, other enzyme or fluorescent fusion proteins, antigens to be used as positive controls, binding ligands for protein arrays), (recombinant) proteins of technical relevance (such as e.g. binding ligands for affinity sorbents, high value enzymes, biocatalysts), and recombinant proteins improving agronomic input or output traits.

Generally speaking, heterologous nucleic acids may be expressed by any appropriate process used in the art or they may be transcribed or expressed as follows:

(i) transient expression of 'naked' DNA e.g. comprising a promoter operably linked to the heterologous sequence of interest, (ii) expression from an expression vector, such as a replicating vector. Generally speaking, those skilled in the art are well able to construct vectors and design protocols for transient recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wiley & Sons, 1992.

(iii) expression from a non-integrating vector.

It will be understood that these categories are not mutually exclusive, for instance because a non-integrating vector may also be an expression vector etc.

As will be appreciated by the skilled artisan, the at least two heterologous nucleic acid sequences coding for a fluorescent marker protein or polypeptide or for an enzyme producing a fluorescent molecule and for the heterologous protein of interest (desired product) may be provided either (i) in polycistronic configuration comprised by a single expression cassette on the same vector, (ii) in a tandem configuration with at least two different expression cassettes on the same vector, or (iii) in at least two different expression cassettes on different vectors, wherein the tandem configuration is preferred.

According to a further aspect, the invention thus also provides a method for the production of at least one desired product preferably selected from the group consisting of heterologous proteins or polypeptides, secondary metabolites, and markers. The method comprises to use the (transgenic) monoclonal plant cell line as established according to the invention in order to produce and accumulate the at least one desired product which is subsequently obtained or isolated from the producing cells or from the cultivation medium.

Thus, in one aspect of the invention, there is disclosed use of a preferably stably transformed monoclonal plant cell line additionally capable of generating mRNA encoding a desired product such as a heterologous target protein generated by transcription from an introduced nucleic acid construct including the target nucleotide sequence operably linked to a promoter.

The "introduced nucleic acid" will thus include the heterologous nucleic acid sequence as a DNA sequence provided in the form of a construct that is capable of giving rise to the production and accumulation of the desired product.

Thus in a preferred aspect of the invention, there is disclosed a method of achieving stable expression of a heterologous nucleotide sequence in a monoclonal plant cell line, which method comprises the step of stably introducing into a target cell at least a first nucleic acid sequence comprising a heterologous nucleotide sequence coding for the desired product.

In one embodiment there is provided a method of generating at least an extracellular heterologous protein, which method comprises the steps of:

(i) stably introducing into a target cell comprised by the starting population of plant cells a first nucleic acid comprising the nucleotide sequence coding for the heterologous protein or desired product;

(ii) preparing protoplasts from plant suspension cells provided from said plant suspension culture, wherein the protoplasts are additionally transformed and capable of (i) producing a fluorescent marker protein or polypeptide and (ii) surviving in presence of a selection agent;

(iii) separating single transformed protoplasts by subjecting the preparation of protoplasts to FACS;

(iv) regenerating a separated single transformed protoplast until the formation of a microcolony or microcallus by co-cultivation in the presence of feeder cell material;

(v) generating a monoclonal callus tissue by (i) transferring the microcolony or microcallus to solid cultivation medium and (ii) cultivating the microcolony or microcallus in the presence of at least one selection agent until the formation of a transgenic callus tissue;

(vi) establishing a transgenic monoclonal plant cell line by transferring the callus tissue to liquid cultivation medium; and (vii) causing or permitting expression from the nucleic acid of the heterologous protein or desired product by providing appropriate cultivation conditions, and (viii) harvesting the accumulated heterologous protein or desired product from the producing cells.

The isolation may be by entirely conventional means, and may or may not entail partial or complete purification.

Naturally, the man skilled in the art will recognize that more than one gene may be used in the, or each, construct. Multiple vectors (each including one or more nucleotide sequences encoding heterologous protein of choice) may be introduced into the target cells as described herein or elsewhere. This may be useful for producing e.g. multiple subunits e.g. of an enzyme.

The fluorescent marker protein or polypeptide can be any protein detectable by fluorescence such as GUS, fluorescent proteins such as GFP or DsRed, luciferase etc. Preferably, the reporter is a non-invasive marker such as DsRed or GFP.

According to a further aspect, the invention provides a method for the identification of higher expressing insertion loci by cell sorting comprising the steps of transforming cells (e.g. as described in Example 1B below) e.g. with a construct containing fluorescent protein 1, and identifying and separating single high fluorescent protein 1 producing cells by FACS including the regeneration to microcolony and suspension culture and the gene exchange e.g. with fluorescent protein 2, and identifying and separating rare gene exchange products.

BRIEF DESCRIPTION OF THE DRAWINGS

FIG. 1 is a schematic drawing illustrating the structure of an expression cassette used for the preparation of a transgenic MTED BY-2 line.

DETAILED DESCRIPTION

The invention will now be further described with reference to the following non-limiting Figures and Examples. Other embodiments of the invention will occur to those skilled in the art in the light of these.

FIG. 1 is a schematic drawing illustrating the structure of an expression cassette used for the preparation of the transgenic MTED BY-2 line as described herein. In particular, the FIGURE illustrates the T-DNA of the pTRAkc::MTED plant expression vector used for the transformation of BY-2 suspension cells.

LB and RB: left and right border of the T-DNA; Pnos and pAnos: promoter and terminator of the nopaline synthase gene; nptII: coding sequence of the neomycine phosphotransferase gene; SAR: scaffold attachment region; P35SS and pA35S: promoter with duplicated enhancer and terminator of the Cauliflower mosaic virus (CaMV) 35S gene; CHS: 5'-UTR of the chalcone synthase from *Petroselinum crispum*; SP: signal peptide; HC and LC: coding sequence of the heavy and light chain of the M12 antibody; TL: 5'-UTR of the tobacco etch virus (TEV); TP: transit peptide; DsRed: coding sequence for the red fluorescent protein from *Discosoma* spec.

EXAMPLES

Example 1

Rapid Generation of Elite-Producing Monoclonal Cell Lines After a Transformation Event
A. Tobacco Cell Culture The wild type suspension culture of *Nicotiana tabacum* cv. Bright Yellow 2 (BY-2) was maintained in darkness under sterile conditions as 50 ml aliquots in 100 ml glass Erlenmeyer flasks at 26° C., with a constant orbital agitation of 180 rpm. The cultivation medium comprised basal MSMO medium (pH 5.8) supplemented with sucrose (3%, w/v) and 1 mg/l 2,4-dichlorophenoxyacetic acid. Subculture was done at day 7 intervals by transfer of 5% (v/v) of the cells into 50 ml fresh medium.

For protoplast preparation the suspension cell culture was subcultured by transfer of 2% (v/v) into 50 ml fresh medium.
B. Accelerated Generation of Transgenic Events for Subsequent Sorting BY-2 wild type suspension cells were cultivated as described in section A. In parallel transgenic *Agrobacterium tumefaciens* harbouring a construct comprising several expression cassettes on the same vector (see FIG. 1) were cultivated in YEB medium containing the appropriate antibiotic (0.5% Nutrient Broth, 0.1% Yeast Extract, 0.5% Peptone, 0.5% Sucrose, 2 mM $MgSO_4$, pH 7.4) on an orbital shaker at 160 rpm and 27° C. to an $OD_{600nm}$ of 1. Three days after subcultivation 3 ml BY-2 wild type cells, 200 nM acetosyringone and 150 µl agrobacteria ($OD_{600nm}=1$) were co-cultivated in Petri dishes in the dark. After 3 days of co-cultivation at room temperature the BY-2 cells were resuspended in 10 ml of BY-2 medium supplemented with 200 mg/l cefotaxime. The cells were transferred to a 50 ml sterile tube and washed twice by centrifugation (850 g, 5 min) in order to remove agrobacteria. After resuspension of the cell pellet cultivation of the transformed BY-2 cells takes place in 100 ml shake flasks using 20-50 ml BY-2 medium supplemented with cefotaxime and a suitable selective agent (180 rpm, 26° C.) After regeneration of a proper suspension (packed cell volume approximately 50-60%) the cells can be subcultured for protoplast preparation (see section C). This method requires 14 to 21 days to establish a transgenic suspension culture that can be used for subsequent protoplast generation (C) and flow cytometric sorting (D).

C. Protoplast Preparation and Cell Wall Regeneration

Actively growing cell cultures were used 3 days after subculture for sedimentation of cells by centrifugation at 850 g for 5 min in sterile conical plastic centrifuge tubes. The supernatant was removed and cells were resuspended in 10 ml of PNT digestion solution (3.6 g/l Kao Michayluk basal salts (Duchefa), 0.4 M sucrose, 0.5 mg/l NAA, 1 mg/l BAP) comprising 1% (w/v) cellulase and 0.3% (w/v) macerozyme. The cell-enzyme suspension was placed into 6 cm Petri dishes sealed with an adhesive tape. Digestion was carried out overnight (16-18 h) at 26° C. in the dark with gentle agitation. Protoplasts were filtered through a 100-µm nylon mesh and subsequently floated to the surface during centrifugation (104 g for 8 min). The pellet and the medium interface were removed and protoplasts washed twice with PNT solution. Protoplasts were resuspended in W5 solution (154 mM NaCl, 125 mM $CaCl_2$, 5 mM KCl, 5 mM glucose, pH 5.6) and sedimented by centrifugation at 76 g for 2 min. Protoplasts were cultured in the modified regeneration medium 8p2c (see table 1 below; optimized from 8p medium) after gentle resuspension. Usually the described procedure resulted in $7 \times 10^5$ protoplasts per ml with an average percentage of 74% viable protoplasts.

Protoplasts were regenerated for 3 days at 26° C. in the dark to initiate cell wall regeneration. The resulting protoplasts were sieved again through a 100-µm nylon mesh and then transferred to a sterile sample introduction tube for FAC sorting. Single protoplasts were sorted into each well of a 96-well microtiter plate containing non-transgenic wild type feeder protoplasts or cells (see section D).

BY-2 wild type protoplasts, which were used as feeder protoplasts were adjusted to approximately $2 \times 10^3$ cells/ml 8p2c medium using a Fuchs-Rosenthal counting chamber. Fifty microliters of these protoplasts were transferred to each well of a 96-well microtiter plate so that approximately 100 wild type feeder protoplasts were transferred into each well.

Table 1: Composition of the 8p2c Medium (pH 5.6)
Kao und Michayluk basal salt mixture (Duchefa)
Kao und Michayluk vitamine solution (Sigma)
    0.02 mg/l p-Aminobenzoic acid
    2 mg/l L-Ascorbic acid
    0.01 mg/l Biotin
    1 mg/l D-Calcium pantothenate
    1 mg/l Choline chloride
    0.4 mg/l Folic acid
    100 mg/l Myo-inositol
    1 mg/l Nicotin amide
    1 mg/l Pyridoxine HCl
    0.2 mg/l Riboflavin
    1 mg/l Thiamine HCl
    0.01 mg/l Vitamin A
    0.02 mg/l Vitamin B12
    0.01 mg/l Vitamin D
Organic acids (pH 5.5 with $NH_4OH$)
    20 mg/l Sodium pyruvate
    40 mg/l Malic acid
    40 mg/l Citric acid
    40 mg/l Fumaric acid
Sugar and sugar alcohols
    0.25 g/l Sucrose
    250 mg/l Mannose
    68.4 g/l Glucose
    250 mg/l Rhamnose
    250 mg/l Fructose
    250 mg/l Cellobiose
    250 mg/l Ribose
    250 mg/l Sorbitol
    250 mg/l Xylose
    250 mg/l Mannitol
Hormones
    0.2 mg/l 2.4-D
    0.5 mg/l Zeatin
    1.0 mg/l NAA
2% (v/v) Coconut water
500 mg/l Casamino acid D. Flow Cytometric Analysis and Sorting The FACS Vantage (DIVA option, BD Bioscience) instrument with a 488 nm/635 nm Argon ion laser was used for sorting of transgenic plant protoplasts. The sheath fluid, a phosphate buffered saline (PBS pH 7.4), was sterilized by autoclaving and by passage through a 0.22 µm filter. Prior to sorting the sample tubes were cleared of residual ethanol by passage of sterile sheath fluid. The cytometer system/sorting settings were aligned using commercial standard autofluorescent calibration particles. The flow sorter was operated at 488 nm with a laser output of 175 mW. Prior to sorting the electronic sort windows were positioned based upon signals collected for forward light scatter, side light scatter and fluorescence of a protoplast culture sample in order to define the strongly fluorescent population. The signals were displayed as dot plots using the DIVA software (BD Bioscience). Sort regions were defined by creating gates first around the population of viable protoplasts and second, based on the first gate, around the population of strongly fluorescent protoplasts. Sorting was performed through a 200-µm flow tip with a system sheath pressure of 4-6 psi, a drop frequency of approx. 7 kHz and a sample flow rate of approx. 1.000 events/sec.

Using the described sorting parameters a plating efficiency of 20% (i.e. 20% of the wells contained intact and viable single sorted protoplasts) was achieved.

E. Regeneration of Single Sorted Protoplasts by Co-Cultivation with Nurse/Feeder Protoplasts Prior to the sorting of highly fluorescent single protoplasts each well of a 96-well microtiter plate was filled with 50 µl of sterile 8p2c regeneration medium containing approx. 100 N. tabacum cv. BY-2 wild type protoplasts as feeder cells. The single sorted transgenic protoplasts were analysed by inverse fluorescence microscopy at different time points to verify single cell deposition after the sorting process and also to monitor the proliferation and microcolony formation (14-20 days after sorting) of the transgenic protoplasts. The cultivation of sorted protoplasts in 96-well plates took place at 26° C. to 27° C. in the dark, the plates were closed with a sterile lid and sealed with adhesive tape.

Transgenic microcolonies were then transferred to solid regeneration medium (0.8% (w/v) agar), containing an antibiotic selection marker (e.g. kanamycin). Therefore, the microcallus tissue including the feeder cells present in the wells were gently resuspended by pipetting and transferred using a pipette with a wide tip end. Subsequently, the wells and also the transferred microcalli on the solid regeneration medium were analysed by inverse fluorescence microscopy to verify the successful transfer of the transgenic and fluorescent microcolonies. Upon the transfer transgenic microcalli were grown for 14-20 days and transferred to fresh plate containing solid regeneration medium including the selection marker. Callus tissue with a size of approximately 2 cm in diameter was used to establish suspension cultures by transfer of the cell material to 5 ml cultivation medium (described in section A) in 50 ml plastic tissue culture flasks. These flasks were cultured as described in section A until the cell suspension was grown up to a packed cell volume of about 50-60% for transfer to 100 ml glass Erlenmeyer flasks. The cultivation of the transgenic monoclonal suspension culture was performed as described in section A.

The described feeder cell strategy permits the regeneration of about 50% of the initially sorted intact and viable single protoplasts (i.e. ca. 10% of the single protoplasts sorted into the wells of a 96-well microtiterplate developed to microcalli).

F. Verification of the Successful Elimination of Feeder Cell Survival During Regeneration of Sorted Single Protoplasts A procedure has been developed that enables the reliable regeneration of single FACS selected protoplasts to monoclonal suspension cultures. Since single protoplasts have to be regenerated after sorting, feeder cells are required to support regeneration and proliferation of sorted single protoplasts. Because the feeder protoplasts are temporarily co-cultivated with sorted fluorescent target protoplasts it is mandatory to exclude a survival of feeder protoplasts during the regeneration of monoclonal cultures.

The potential contamination of single sorted transgenic and fluorescent BY-2 cells with feeder protoplasts has been investigated. Transgenic cells have been transformed with a construct containing a GFP-KDEL expression cassette and an AHAS selection marker (conferring Imazethapyr resistance). Single BY-2 protoplasts transformed with this construct and producing GFP were sorted into 96-well plates containing protoplasts of a transgenic cell line containing a DsRed expression cassette and a nptII selection marker (conferring kanamycin resistance). In a second experiment, single BY-2 protoplasts transformed with the DsRed expression cassette and a nptII selection marker were sorted into 96-well plates containing protoplasts of the transgenic cell line producing GFP. After regeneration the resultant GFP and DsRed fluorescent cultures were analyzed with respect to their resistance towards imazethapyr or kanamycin and their fluorescence (green versus red). Callus tissue from both approaches was plated on selection medium containing either 1.5 μM imazethapyr or 100 mg/L kanamycin. Cell growth was evaluated visually after 14 days of incubation. All of the tested calli (20 in total) grew exclusively on medium plates containing their specific selective agent. In brief, GFP/AHAS transformed calli grew on imazethapyr but not on kanamycin containing plates whereas DsRed/kanamycin transformed calli grew only on kanamycin plates. This observation clearly demonstrated that regenerated transgenic cell lines were not contaminated with the respective feeder cell line. A potential contamination with feeder cells was additionally assessed by flow cytometric analysis. The regenerated GFP and DsRed suspension cultures were analyzed with respect to their optical properties elicited by the fluorescent proteins GFP or DsRed, respectively. This observation clearly demonstrated that regenerated transgenic cell lines were not contaminated with the respective feeder cell line. All tested BY-2 cultures showed exclusively the expected fluorescence pattern. Cultures established after sorting of GFP transformed cells show only green fluorescence while cultures producing DsRed were detected exclusively in the red fluorescence channel. In the case of a contamination with feeder cells a fluorescence signal in both channels would have been expected. The result of the cytometric analysis confirmed the efficient removal of feeder cells on selection plates as demonstrated before by the resistance test.

G. Analysis of Monoclonal Transgenic Suspension Cultures

The monoclonal suspension cultures were first analysed regarding their percentage of highly fluorescent cells. Therefore, protoplasts were prepared as described in section C. For the flow cytometric determination of the portion of fluorescent protoplasts the FACS Calibur Instrument (BD Bioscience) was used. Based on BY-2 wild type protoplasts the setting parameters (e.g. amplification of light and fluorescence scatter multipliers) were adjusted and the samples were measured. After gating the viable population, the distribution of this population in the fluorescence channel was used to set a threshold, which excluded all background signals caused by the wild type autofluorescence. According to this threshold the percentage of fluorescent protoplasts within the improved protoplast cultures derived from a single protoplast was calculated. Flow cytometric analyses of the monoclonal suspension cultures producing the recombinant DsRed protein displayed homogeneously distributed cells of similar and strong fluorescence intensities (narrow fluorescent peaks). The calculation of the DsRed fluorescent cell portions resulted in percentages ranging between 78-88% strongly fluorescent cells.

The accumulation levels for the recombinant protein can be determined by different procedures (e.g. enzyme linked immunosorbent assay (ELISA)). Therefore, the cells were centrifuged (850 g, 5 min), resuspended in 3 Vol. extraction buffer (PBS pH 6, 5 mM 2-mercaptoethanol, 5 mM EDTA, 10 mM ascorbic acid) and disrupted by sonication. The extract was separated from cell debris by another centrifugation step (20 min., 16 000 g) and used for analysis. Immunological analysis of the M12 antibody accumulation in 5 dpi cell extracts of suspension cultures transformed with pTRAkc:MTED revealed up to 118±20 μg/g fresh weight (1.5 fold higher than using the conventional generation method i.e. callus generation and screening).

Example 2

Generation of Monoclonal Cell Lines from a Heterogeneous Transgenic Suspension Culture A. Tobacco Cell Culture The transgenic *Nicotiana tabacum* cv. Bright Yellow 2 (BY-2) suspension culture MTED#18 producing the ER-retarded human full-size IgG1 antibody M12 and the plastid targeted fluorescent protein DsRed was maintained in the dark under sterile conditions as 50 ml aliquots in 100 ml glass Erlenmeyer flasks at 26° C., with a constant orbital agitation of 180 rpm. BY-2 wild type cells were cultivated under the same conditions as control. The cultivation medium comprised basal MSMO medium at pH 5.8 supplemented with sucrose (3%, w/v) and 1 mg/l 2,4-dichlorophenoxyacetic acid. Subculture was done at day 7 intervals by transfer of 5% (v/v) of the cells into 50 ml fresh medium.

The transgenic suspension culture has been generated by *Agrobacterium*-mediated transformation of *N. tabacum* cv. BY-2 cells followed by an antibiotic based selection and subsequent separation of transformed callus tissue. The callus tissues were screened according to their antibody production by immunological assays (Dotblot and ELISA) and the best candidate was used for suspension culture establishment (=cell line MTED#18). The specific M12 antibody production of the parental MTED#18 culture was 13 µg/g fresh cell weight (10 mg/L). Flow cytometric analysis revealed that the transgenic culture consists of two subpopulations with only 24% of the viable population producing the fluorescent marker protein DsRed.

For protoplast preparation the suspension cell culture was subcultured by transfer of 2% (v/v) into 50 ml fresh medium.

B. Protoplast Preparation and Cell Wall Regeneration

See example 1, section C.

Usually the described procedure resulted in $5 \times 10^5$ protoplasts per ml with an average percentage of 62.2 of viable transgenic protoplasts.

C. Flow Cytometric Analysis and Sorting

The instrument settings and pre-arrangements were done as described in example 1, section D.

Single strongly fluorescent plant protoplasts (1-2% of all sorted protoplasts) were sorted into cell deposition device (i.e. microtiter plates) in single cell mode. One protoplast per well, consistent to the second gated criteria, was sorted into 96-well plates filled with 50 µl of sterile 8p2c regeneration medium containing approx. 100 wild type protoplasts as feeders. The 96-well plates were closed using a sterile lid and sealed by an adhesive tape. The actual number of recovered protoplasts was determined by inverse fluorescence microscopy. The flow cytometric sorting of protoplasts in single cell mode resulted in a plating efficiency of approximately 20% wells containing one intact and viable protoplast per well.

D. Regeneration of Sorted Protoplasts at Low Densities

The regeneration of single sorted protoplasts was performed as described in example 1, section E.

The flow cytometric sorting of highly fluorescent protoplasts in the single cell mode resulted in approximately 20% of the wells containing only one sorted protoplast. 50% of these single protoplasts started proliferation and could be used to establish suspension cultures.

E. Analysis of Monoclonal Transgenic Suspension Cultures

To determine the percentage of fluorescent protoplasts in improved suspension cultures derived from a single protoplast a flow cytometric analysis was performed as described before (experiment 1, section D). The M12 antibody accumulation levels were determined by an enzyme linked immunosorbent assay (ELISA). Therefore, the suspension cells were centrifuged (850 g, 5 min), resuspended in 3 Vol. extraction buffer (PBS pH 6, 5 mM 2-mercaptoethanol, 5 mM EDTA, 10 mM ascorbic acid) and disrupted by sonication. The extract was separated from cell debris by a centrifugation step (20 min, 16000 g) and used for analysis. Due to the chosen set up (Fc capture and LC detection) only fully assembled antibodies were detected.

After one FACS round the monoclonal suspension cultures showed significantly improved accumulation levels for both recombinant proteins: 3.7-fold enriched percentage of DsRed fluorescent cells (90%) and 11-fold increase of the M12 antibody (145 µg/g fresh weight or 9.3 fold on mg/L level (93 mg/L)) when compared to the parental suspension culture.

F. Repetition of Suspension Culture Improvement

In order to further increase and stabilize recombinant protein productivity of transgenic monoclonal suspension cultures steps B-E can be repeated. The same conditions for protoplast generation sorting and regeneration as described before were applied.

The second sorting round resulted in a further increase of antibody accumulation: 182 µg/g fresh weight or 113 mg/L, which is a 14-fold and 11.3-fold increase compared to the parental culture.

A third round of sorting of the best producing $2^{nd}$ generation monoclonals resulted in $3^{rd}$ generation monoclonal cultures producing similar accumulation levels indicating that the maximum level was achieved.

G. Stability of Elite Producing Monoclonal Cultures in Terms of Target Protein Productivity The stability of FACS derived monoclonal cell lines was investigated exemplary for 3 monoclonal lines. Monoclonal cell lines were subcultured in a 7 day cycle (refer to example 1, section A) while both recombinant target proteins were measured at 2 month intervals always on day 5 after subculture. Over a period of 12 month it has been demonstrated for the $1^{st}$ generation of monoclonal cultures that these cultures still produce high and stable amounts of the M12 antibody per gram fresh weight. Only slight variations of antibody levels in the bi-monthly sampling intervals (caused by cell cultivation variations) were observed.

Analysis of the $2^{nd}$ generation monoclonals verified cell line stability by showing similar or slightly increased accumulation levels of both recombinant proteins M12 antibody and DsRed compared to the $1^{st}$ generation monoclonal culture they were derived from. Over all the analyzed monoclonal cultures of the $2^{nd}$ generation appear more stable in terms of target protein production (less variations in bi-monthly sampling intervals) compared to $1^{st}$ generation monoclonal cultures. During a period of 12 month two of the three analyzed monoclonal cultures were found to be highly stable regarding their percentage of DsRed fluorescent cells in the total population as well as M12 antibody accumulation.

The invention claimed is:

1. A method for the generation of a monoclonal plant cell line from a heterogeneous population of plant cells, comprising the following steps:

(a) providing a heterogeneous population of plant cells;

(b) preparing a heterogeneous population of protoplasts from the heterogeneous population of plant cells, wherein at least one of the protoplasts from the prepared heterogeneous population of protoplasts is transformed with at least one expression vector encoding at least one fluorescent protein and a resistance against at least one selection agent;

(c) initiating cell wall regeneration in said heterogeneous population of protoplasts for fluorescence activated cell sorting (FACS);

(d) providing a cell deposition device containing feeder cells in liquid medium containing wells;

(e) sorting by FACS the prepared at least one protoplast from the heterogeneous population of protoplasts in which the cell wall regeneration has been initiated, wherein said at least one protoplast is highly fluorescent;

(f) separating the sorted at least one protoplast into at least one different liquid medium-containing well containing the feeder cells for monoclonal plant cell generation such that said at least one well for monoclonal plant cell line generation contains a single prepared protoplast permitted to directly contact the feeder cells;

(g) regenerating the single separated protoplast from said at least one well into a microcolony by co-cultivating the separated protoplast in the same well as the feeder cells; and (h) removing the microcolony from the feeder cells and cultivating the microcolony in the presence of said at least one selection agent against which said at least one protoplast is transformed with said at least one expression vector encoding a resistance until a monoclonal plant cell line from said at least one protoplast is established.

2. The method according to claim 1, further comprising regenerating the monoclonal plant cell line established in step (h) into whole fertile plants.

3. The method according to claim 1, wherein the at least one protoplast of step (b) is additionally transformed to produce one or more desired products selected from the group consisting of heterologous proteins or polypeptides, secondary metabolites, and markers for diagnostic or analytic purposes and wherein the monoclonal plant cell line of step (h) produces said one or more desired products.

4. The method according to claim 1, wherein the heterogeneous population of plant cells is provided from an already transgenic heterogeneous plant suspension culture comprising transgenic cells.

5. The method according to claim 1, wherein the at least one protoplast is transformed with a resistance against at least one antibiotic or herbicide selection agent.

6. The method according to claim 1, wherein said monoclonal plant cell line is stable for at least 2 months.

7. The method according to claim 3, wherein said monoclonal plant cell line produces stable amounts of said one or more desired products for at least 2 months.

8. The method according to claim 1, wherein said monoclonal plant cell line is stable for at least 12 months.

9. The method according to claim 3, wherein said monoclonal plant cell line produces stable amounts of said one or more desired products for at least 12 months.

* * * * *